United States Patent [19]

Stevens

[11] Patent Number: 5,536,261
[45] Date of Patent: Jul. 16, 1996

[54] METHOD AND CLOSED TIP EFFECT CATHETER APPARATUS FOR USE IN ANGIOGRAPHY

[76] Inventor: Robert C. Stevens, 18265 NW. Hwy. 335, Williston, Fla. 32696

[21] Appl. No.: 299,759

[22] Filed: Sep. 1, 1994

[51] Int. Cl.$^6$ .................. A61M 25/14; A61M 25/09; A61M 39/20
[52] U.S. Cl. ........................ 604/280; 604/256
[58] Field of Search ................. 604/282, 167, 604/256, 280

[56] References Cited

U.S. PATENT DOCUMENTS

| | | | |
|---|---|---|---|
| 4,673,393 | 6/1987 | Suzuki et al. | 604/167 |
| 4,735,620 | 4/1988 | Ruiz . | |
| 4,755,176 | 7/1988 | patel . | |
| 4,798,594 | 1/1989 | Hillstead | 604/167 |
| 4,846,814 | 7/1989 | Ruiz . | |
| 4,886,506 | 12/1989 | Lovgren et al. | 604/280 |
| 4,961,731 | 10/1990 | Budicky et al. | 604/280 |
| 5,041,095 | 8/1991 | Littrell | 604/167 |
| 5,053,013 | 10/1991 | Ensminger et al. | 604/167 |
| 5,057,083 | 10/1991 | Gellman | 604/280 |
| 5,061,257 | 10/1991 | Martinez et al. . | |
| 5,069,673 | 12/1991 | Schwab | 604/280 |
| 5,147,332 | 9/1992 | Moorehead | 604/280 |
| 5,167,637 | 12/1992 | Okada et al. | 604/167 |
| 5,171,232 | 12/1992 | Castillo et al. | 604/280 |
| 5,180,387 | 1/1993 | Ghajar et al. . | |
| 5,201,723 | 4/1993 | Quinn . | |
| 5,201,724 | 4/1993 | Hukins et al. | 604/280 |
| 5,221,257 | 6/1993 | Rosenbloom et al. | 604/280 |
| 5,236,424 | 8/1993 | Imran | 604/280 |
| 5,267,966 | 12/1993 | Paul | 604/167 |
| 5,282,784 | 2/1994 | Willard | 604/280 |
| 5,300,048 | 4/1994 | Drewes, Jr. | 604/280 |
| 5,304,156 | 4/1994 | Sylvannowicz et al. | 604/167 |
| 5,334,154 | 8/1994 | Samson et al. | 604/280 |
| 5,423,764 | 6/1995 | Fry | 604/280 |
| 5,425,723 | 6/1995 | Wong | 604/260 |

OTHER PUBLICATIONS

"Cordis Ducor Catheters and the Angiographic Ssystem", selected pages from equipment catalog, 1982–1983, pp. 9–26.

Primary Examiner—Paul J. Hirsch
Attorney, Agent, or Firm—Fay, Sharpe, Beall, Fagan, Minnich & McKee

[57] ABSTRACT

A catheter apparatus includes an elongate hollow tubular body portion with multiple side holes a sealing member on its distal end for preventing flow from the distal end. All flow is thereby directed through the multiple side holes. The sealing member is designed to be punctured or selectively opened by a guide wire if the need arises. The tip sealing member is further design to "reseal" if it becomes necessary to perforate the seal. This "resealing" greatly reduces the end flow and encourages lateral flow through the multiple side holes.

7 Claims, 1 Drawing Sheet

METHOD AND CLOSED TIP EFFECT CATHETER APPARATUS FOR USE IN ANGIOGRAPHY

BACKGROUND OF THE INVENTION

This application pertains to the art of catheters and the use thereof and more particularly relates to angiographic catheters and their use. The invention is particularly applicable to closed tip effect angiographic catheters and will be described with particular reference thereto. It is to be appreciated, however, that the invention has broader applications such as for use with any catheters or other conduits having an open ended tip through which opaque media can be injected into the desired blood vessels or target areas or through which pressures within the blood vessels or target areas may be monitored.

Most angiographic catheters have heretofore included an open ended tip through which an opaque media such as a dye is injected under pressure into a blood vessel or artery. The opening is also used in certain situations to monitor the fluid pressures within the blood vessel where necessary. The opening on the catheter tip proved useful in applications where a guide wire is used to aide in advancing the catheter tip to the desired target vessel. The guide wire itself is positioned within the vessel e.g. femoral artery via the percutaneous technique.

The percutaneous or Seldinger technique involves first puncturing through the outer body tissues and into the vessel of choice such as the femoral artery. After the needle is placed within the vessel of choice, a guide wire, usually formed of stainless steel, is passed through the needle opening and into the vessel. Next, the needle is withdrawn from the vessel and out of the body over the guide which remains lodged in part within the vessel. After the needle has been removed, the open tip end of the catheter is threaded over the guide and into the blood vessel. The guide, at this point, can be withdrawn through the hollow tubular opening of the catheter. At this point in the procedure, a lead end of the catheter is inserted into the vascular system without the necessity to cut open or otherwise sever the blood vessel to gain entry. Often times, however, the guide and catheter are advanced together or otherwise in cooperative unison in order to position the distal end of the open tip catheter through the branching vessel openings to the area to be studied.

In heart studies such as investigations of the coronary arteries, it is necessary most often to study the left ventricle. In this particular application, the flexible catheter may have to be passed over a more rigid guide wire in order to cross a stenotic heart valve and into the ventricle whereat a large amount of opaque media is delivered in a very short period of time. One undesirable result of this large amount of fluid delivery over a short period of time is that the catheter tip "jets" or "whips" within the ventricle. Such movement can dislodge the catheter tip from the ventricle or worse, cause damage to the heart.

In order to provide a catheter which does not exhibit the "jetting" or "whipping" such as present in the open tip catheters, a "pigtail" or curved tip catheter is being used. Although these catheters address the problem of whipping, they are perhaps the most dangerous of all catheters because of their geometry. Numerous side holes are formed in the tip of the catheter in addition to the open tip end which is usually several centimeters downstream of the side holes. Although a saline drip or flush is used to clear the openings in the catheter and prevent clotting as discussed in conjunction with the open tip catheters above, it is not always possible to entirely flush or clear the "pigtail" area. This is because the cross-sectional area of the side hole openings of non-whip catheters such as the pigtail are about twenty times greater than the tip end opening. Accordingly, most of the saline drip or flush never realizes an exit through the tip opening.

The relative ratios of the hole openings in the pigtail catheters are deliberate. The small tip end opening combined with the 360° loop of the tip forward of the side holes encourages a lateral fluid flow. This arrangement maintains the catheter in a stationary position as the opaque media is injected therethrough.

The principle problem with pigtail type catheters is that it is difficult to maintain the catheter tip free of blood clots forming thereat. In addition, the pigtail catheters are rather difficult to pass over a guide wire which is used to introduce the catheter into the entry vessel.

The present invention contemplates a new and improved closed tip effect angiographic catheter apparatus which overcomes all of the above referred problems and others and provides an angiographic catheter combining the best features of both the closed and open tip catheters described above.

BRIEF SUMMARY OF THE INVENTION

In accordance with the present invention, there is provided a catheter apparatus including an elongate hollow tubular body portion formed of a flexible polymeric material and adapted to conduct a fluid flow therethrough. A thin flexible sealing member is located on a distal end of the elongate hollow tubular body portion for restricting the fluid flow through the tip end. The sealing member is adapted for remaining closed even under pressure. This encourages lateral flow which is most desirable.

Further in accordance with the invention, the sealing member on the distal end of the elongate hollow tubular body portion is adapted to be pierced if needed by a guide wire within the tubular body portion during a surgical procedure. The sealing member forms a fluid tight seal between the control wire and the catheter lumen.

The primary object of the instant invention is to provide an improved angiographic catheter that exhibits the best properties of both closed tip catheters as well as open tip devices.

A further object is the provision of a catheter having a sealing member on the distal end of the body portion that is adapted to be pierced by a guide wire where desired. This is useful in procedures such as where a guide wire must be used to cross a diseased or calcified heart valve where traditional catheters have difficulty penetrating.

Another object of the invention is the provision of a catheter tip which reduces or eliminates the quantity of fluid lost through the tip end. This encourages lateral flow through the side holes. With the tip end closed a saline drip or flushing will wash out the inside of the tip area and prevent clots from forming.

Still other objects and advantages of the invention will become apparent to those skilled in the art upon a reading and understanding of the following detailed description.

BRIEF DESCRIPTION OF THE DRAWINGS

The invention may take physical form in certain parts and arrangements of parts, the preferred embodiments and meth

DETAILED DESCRIPTION OF THE PREFERRED EMBODIMENTS AND METHODS

Figure 1:
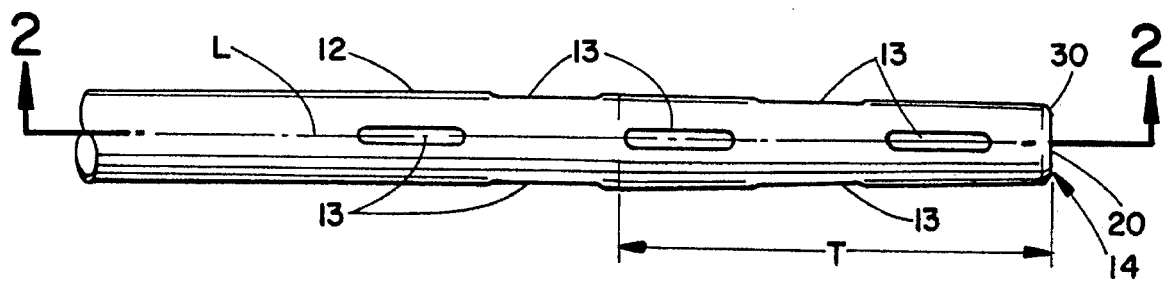
- FIG. 1 is a side view of the distal end region of an angiographic catheter in accordance with the present invention.

Referring now to the drawings wherein the showings are for the purposes of illustrating the preferred embodiments and methods of the invention only and not for the purposes of limiting same, the figures show the end portion of an angiographic catheter 10 including an elongate hollow tubular body portion 12 formed of a flexible polymeric material and having a plurality of side discharge holes 13. In the usual manner, a coupling member is arranged on the proximal end of the tubular body portion 12 (not shown) for connection to a liquid injection device (not shown).

The tubular body portion 12 of the catheter 10 comprises a distal tip 14 which obstructs the flow of fluid through the distal tip by means of a sealing member 20. As shown in the figure, the sealing member 20 is preferably essentially a membrane lying substantially in a plane transverse to the longitudinal axis L of the catheter 10. In the preferred embodiment, the sealing member 20 is formed of a softer polymeric material than the tubular body portion 12 of the catheter 10. Preferably, the softer polymeric material is polyurethane manufactured by B. F. Goodrich under the trade name Estane. This material exhibits a shore durometer of about 80A.

Figure 2:
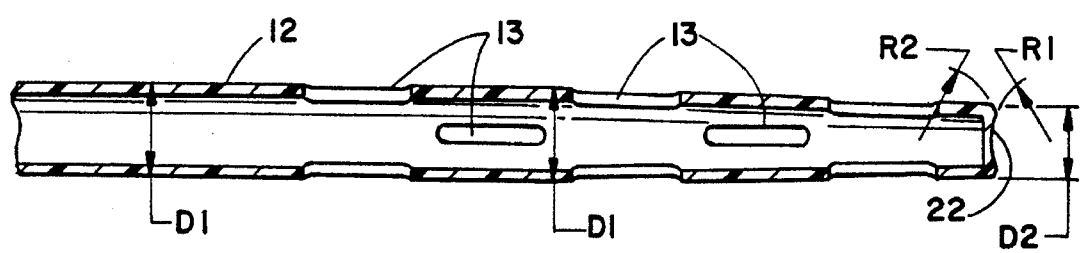
FIG. 2 is a longitudinal cross-sectional view of the angiographic catheter of FIG. 1 taken along line 2—2.

With reference now to FIG. 2 in conjunction with FIG. 1, a cross-sectional view of the angiographic catheter is illustrated whereby it can be seen that the sealing member 20, although substantially overall planar, forms a concave surface 22 at the distal tip 14 of the catheter 10. The concave surface defines a radius R1 of ¾ in. Since the surface is concave, the sealing member 20 is thinnest and, therefore, least resilient at its center which is preferably coincident with the central longitudinal axis L of the catheter 10.

The sealing member 20 attaches to the distal tip 14 of the catheter 10 around its periphery at an annular shoulder region 30 which is preferably formed of the same polymeric material as the tubular body portion 12. The shoulder region 30 is fashioned to form a blunt or "bullet" frustoconical member adapted to be routed through blood vessels without producing damage by gouging or scratching. According to the preferred embodiment, the annular shoulder region 30 defines a second radius R2 of ½ in.

With continued reference to FIGS. 1 and 2, the tubular body portion 12 of the catheter be is gradually evenly tapered along a linear longitudinal region T for the purposes of increasing the flexibility of the distal tip 14 while, at the same time, permitting the catheter to be smoothly inserted first into then through the various branching blood vessels and arteries. The taper is slight but exaggerated in the figure for ease of understanding. Preferably, the outer diameter D1 of the typical tubular body portion is 0.092 in. At the distal tip 14 the outer diameter D2 of the catheter is 0.072 in. The tapered region T extends for 3 in. proximally from the distal tip.

Figure 2A:
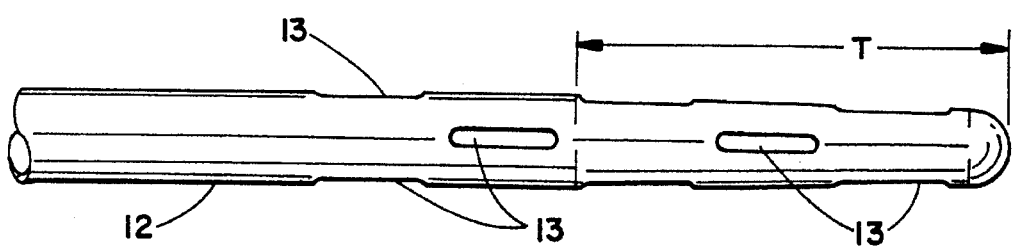
FIG. 2a is a side view like FIG. 1 but showing a modified form of the invention.

FIG. 2a shows an alternative form wherein the sealing member 20 can have a convex configuration. It is preferred that the center of the sealing member 20 be the thinnest as in the FIG. 2 showing.

Figure 3:
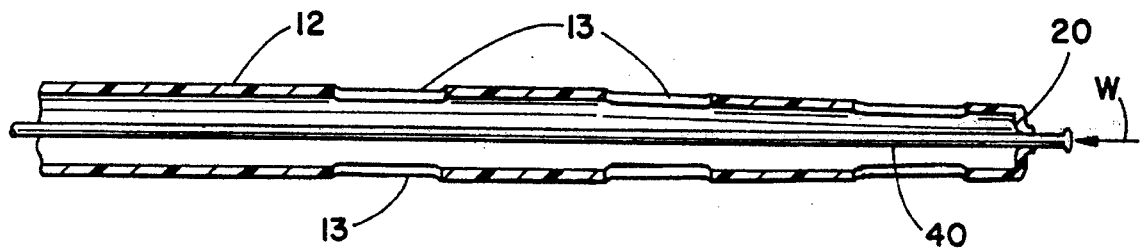
FIG. 3 is a longitudinal cross-sectional view of the angiographic catheter of FIG. 1 taken along line 2—2 with a guide wire received therein; preferred embodiment of present invention.
Figure 2B:
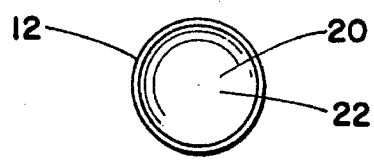
FIG. 2b is an end view of the device of FIG. 2.

FIG. 3 illustrates a cross-sectional view of the catheter of FIG. 1 with a guide wire 40 received therein and extending through the sealing member 20. The guide wire 40 is of the general type known in the art and forms no part of the instant invention. In any case, as can be seen in that figure, the sealing member 20 is perforated by the guide wire 40. Since the sealing member 20 is formed of softer polymeric material than the tubular body portion 12, a fluid tight seal is created between the perforated sealing member 20 and the guide wire 40 due to the elastic resiliency of the polymeric material. When the guide wire 40 is withdrawn from the catheter 10 in the direction marked W in the drawing, the sealing member 20 is adapted to spring back to its approximate original confirmation. The catheter thereby becomes once again a closed tip device.

With the advent of the catheter sheath introducer, it is now possible to pass a closed tip catheter through the various blood vessels of the human body without the use of a guide wire at all. The closed tip catheter according to the preferred embodiment such as shown in FIGS. 1 and 2 can cooperate with a catheter sheath introducer for movement through the various blood vessels. However, there are instances in many procedures where a more rigid tool such as a guide wire must be used such as to cross a diseased or calcified heart valve. In that case, it becomes necessary to open the tip of the catheter in order to pass a guide wire therethrough. Heretofore there have been no devices capable of this dual function.

As illustrated in FIG. 3, the sealing member 20 is fashioned to form a membrane over the face of distal tip 14 of the catheter. The member is resiliently deformable by the leading edge of the guide wire 40. The membrane of the sealing member 20 originally remains intact as illustrated in FIG. 2 and the overall catheter acts as a closed tip catheter until a guide wire 40 is passed through the catheter to perforate the sealing member 20 such as shown in FIG. 3. When the sealing member 20 is perforated, it snugly engages the outer surface of the guide wire 40 and substantially closes upon itself upon withdrawal of the guide wire in the direction marked W.

In use, the tubular tip portion of the catheter is disposed near a catheterization target site. Next, a guide wire is received into the hollow tubular body portion 12 of the catheter 10 along the longitudinal axis L. The sealing member 20 is opened by the advancing leading edge of the guide wire 40. Next, the leading edge of the guide wire is advanced such as through a diseased or calcified heart valve to the target such as a ventricle through the opened sealing member. Once the lead edge of the guide wire 40 is properly in place within the target ventricle, the catheter 10 is advanced over the guide wire held stationary and toward the target ventricle through the diseased or calcified heart valve. The guide wire 40 is retracted from the tubular body portion 12 and is withdrawn from the distal tip 14. The resiliently deformable sealing member 20 snaps back closed in a ready condition for the subsequent injection of pressurized opaque media through the lumen of the catheter 10 and out the side holes 13 of the distal tip 14 into the target site such as the heart ventricle.

The sealing member, of course, can be applied to any angiographic catheter regardless of the shape. The catheter tip may be a single curve, a double curve, or "pigtail" configuration.

The invention has been described with reference to the preferred embodiments. Modifications and alterations will occur to others upon reading and understand of this specification. It is my intention to include all such modifications and alterations insofar as they come within the scope of the appended claims or equivalents thereof.

Having thus described the invention, applicant now claims:

1. A catheterization method comprising the steps of:

providing an elongate tubular catheter having a hollow tubular body portion formed of a flexible polymeric material and a tubular tip portion on a distal end of the elongate tubular catheter, the tubular tip portion having a side wall and a tip end, the side wall having side holes and the tip end being sealed by a thin unperforated sealing member to prevent fluid flow through the tip end portion;

disposing said tubular tip portion near a catheterization target site;

receiving a guide wire into the hollow tubular body portion along the longitudinal axis of the elongate tubular catheter;

opening the sealing member in the tip end by perforating it with a lead edge of the guide wire;

advancing the lead edge of the guide wire to the target site through the perforated sealing member;

disposing the tubular tip portion at the target site by effecting relative motion between the elongate tubular catheter and the guide wire;

retracting the guide wire from the elongate tubular catheter to allow the perforated tip end sealing member to close; and, passing a fluid through the hollow tubular body portion through the side holes of the tip portion.

2. The method according to claim 1, wherein the step of perforating the sealing member includes tearing the sealing member with the lead edge of the guide wire.

3. A catheter apparatus comprising:

an elongate hollow tubular body portion having a continuous side wall formed of a flexible polymeric material and adapted to conduct a fluid flow therethrough; and, an unperforated sealing member on a distal end of said elongate hollow tubular body portion for restricting said fluid flow through the tip and resisting flow even under pressure, said unperforated sealing member being thinner than the continuous side wall of the tubular body portion.

4. The apparatus according to claim 3, wherein the sealing member is formed of the same flexible polymeric material as said elongated hollow tubular body portion.

5. The apparatus according to claim 3, wherein the sealing member is sufficiently thin and resilient as to permit it to be pierced by a guide wire manually movable to within the tubular body portion and fluid tight seal about said guide wire.

6. The apparatus according to claim 5, wherein said sealing member is formed of a softer flexible polymeric material than said elongate hollow tubular body portion.

7. A catheterization method comprising the steps of:

providing an elongate tubular catheter having a hollow tubular body portion and a tubular tip portion having a side wall on a distal end of the elongate tubular catheter, the side wall having side holes, the tubular tip portion being selectively sealed by a sealing member to selectively prevent fluid flow through the distal tip of the tubular portion;

disposing said tubular tip portion at a catheterization target site;

passing a fluid flow through the hollow tubular body portion; and, passing said fluid out the side holes of the tip.

* * * * *